United States Patent [19]
John

[11] Patent Number: 6,067,467
[45] Date of Patent: May 23, 2000

[54] EEG OPERATIVE AND POST-OPERATIVE PATIENT MONITORING METHOD

[75] Inventor: Erwin Roy John, Mamaroneck, N.Y.

[73] Assignee: New York University, New York, N.Y.

[21] Appl. No.: 09/217,010

[22] Filed: Dec. 21, 1998

Related U.S. Application Data

[63] Continuation-in-part of application No. 08/996,003, Dec. 22, 1997, abandoned, which is a continuation-in-part of application No. 08/612,094, Mar. 7, 1996, Pat. No. 5,699,808, which is a continuation-in-part of application No. 08/192,836, Feb. 7, 1994, abandoned.

[51] Int. Cl.[7] ................................... A61B 5/04
[52] U.S. Cl. .................. 600/544; 546/485; 546/529; 546/509
[58] Field of Search .................. 600/483, 484, 600/544, 546, 545, 485, 529, 509

[56] References Cited

U.S. PATENT DOCUMENTS

| | | |
|---|---|---|
| 4,788,982 | 12/1988 | Gedeon et al. . |
| 4,846,190 | 7/1989 | John . |
| 4,869,264 | 9/1989 | Silberstein . |
| 5,010,891 | 4/1991 | Chamoun . |
| 5,195,531 | 3/1993 | Bennett . |
| 5,320,109 | 6/1994 | Chamoun et al. . |

*Primary Examiner*—Linda C. M. Dvorak
*Assistant Examiner*—Bryan K. Yarnell
*Attorney, Agent, or Firm*—Eliot S. Gerber

[57] ABSTRACT

An electrocephalograph (EEG) method is provided to monitor patients during and after medical operations. An anesthesiologist administers sufficient anesthetics to cause the patient to attain the desired plane of anesthesia. The patient's brain waves, both ongoing and evoked by stimuli, are amplified, digitized and recorded. That pre-operative set of brain wave data is compared to a set of the patient's brain wave data obtained during the operation in order to determine if additional, or less, anesthesia is required, paying particular attention to the relative power in the theta band, as an indication of brain blood flow, and prolongations of the latency periods under brain stem stimuli, as an indication of the patient's ability to feel pain. A set of neurometric features are extracted, converted into a normalized statistical score, a discriminant score is thereby developed and the discriminant score converted to a patient state index using probability functions.

29 Claims, 6 Drawing Sheets

EEG OPERATIVE AND POST-OPERATIVE PATIENT MONITORING METHOD

RELATED APPLICATIONS

This application is a continuation-in-part application partly based on application Ser. No. 08/996,003, filed Dec. 22, 1997, now abandoned, which was a continuation-in-part application partly based on application Ser. No. 08/612,094, filed Mar. 7, 1996, now U.S. Pat. No. 5,699,808, which was a continuation-in-part application partly based on Ser. No. 08/192,836, filed Feb. 7, 1994, now abandoned.

FIELD OF THE INVENTION

The present invention relates to medical systems and methods and more particularly to an electroencephalograph (EEG) based system for patient monitoring of anesthesia during surgical operations and in recovery and intensive care.

BACKGROUND OF THE INVENTION

At the present time anesthetics (drugs which induce loss of sensation) are often used for surgical operations. A general anesthetic should cause a progressive depression of the central nervous system and cause the patient to lose consciousness. In contrast, a local anesthetic will affect sensation at the region to which it is applied.

Generally, the patient, prior to the operation, is anesthetized by a specialized medical practitioner ("anesthesiologist") who administers one or more volatile liquids or gases, such as nitrous oxide, ethylene, cyclopropane, ether, chloroform, halothane, etc. Alternatively, non-volatile drugs may be administered by injection or intravenous infusion, such drugs including pentothal, evipal and procaine.

Some of the objectives of a correctly administered general anesthetic are as follows:

First, the patient should be sufficiently anesthetized so that his/her movements are blocked. If the patient's movements are not sufficiently blocked, the patient may begin to "twitch" (involuntary muscle reflexes) during the operation, which may move or disturb the operating field (area being operated upon). Such blockage of movement occurs with a blockade of the neuromuscular junction with muscle relaxants and may also be accomplished by certain actions of anesthetic agents on the central nervous system.

Secondly, the patient should be sufficiently unconscious so as to feel no pain and be unaware of the operation. Patients have sued for medical malpractice because they felt pain during the operation or were aware of the surgical procedure.

Thirdly, the anesthesia should not be administered in an amount so as to lower blood pressure to the point where blood flow to the brain may be reduced to a dangerous extent (generally below 50 mm Hg for mean arterial pressure (MAP)), i.e., cause cerebral ischemia and hypoxia. For example, if the blood pressure is too low for over 10 minutes, the patient may not regain consciousness or be cognitively or otherwise impaired.

A skilled anesthesiologist may monitor the vital signals (breathing, blood pressure, etc.) of the patient to determine if more, or less, anesthetic is required. Often he/she looks into the patient's eyes to determine the extent of the dilation of the pupils or checks the lash reflex as an indication of the level (depth) of the effect of the anesthesia (called "plane of anesthesia"). However, there may be a number of problems with such complete reliance on the skill and attention of the anesthesiologist. In some operations, such as some heart surgery, the head is covered so that the patient's eyes cannot be viewed. Some operations may be prolonged, for example, 10 to 15 hours, so the attention of the anesthesia nurse or anesthesiologist may flag or fail.

It has been suggested that some of these problems would be avoided by having a computer system determine the best anesthetic mix and the amount of each anesthetic based on the patient's sex, age, weight, physical condition and the type of operation. However, it is believed that such a computer determination would not be successful due to the great diversity of response among individuals to different anesthetics, variations in premedications or mixtures of agents.

The inventor's prior U.S. Pat. No. 4,557,270, entitled "Electroencephalographic System For Intra-Operative Open-Heart Surgery", incorporated by reference herein, describes an electroencephalograph (EEG) system used intra-operatively in cardiovascular (open-heart) operations using a heart-lung machine (cardiopulmonary by-pass) such as heart valve replacement surgery. That system, called "CIMON" (Cardiovascular Intraoperative Monitor) is presently being sold by Cadwell Laboratories, Kennewick, Washington, and has been successfully used in many heart operations. However, the CIMON system, with its attention to the heart-pump rate, etc., is not used in general surgery.

In Chamoun U.S. Pat. No. 5,010,891 EEG potentials from a group of healthy surgical patients are recorded (col. 14, lines 32–34). A "reference array" is obtained of the most significant locations and an "autobispectral density index" is defined based on the recordings from a normal group. Each normal group index is then compared to the index of the patient under review. However, as explained above, the comparison of patients with a normal group, in itself, is not believed to provide reliable information in the surgical context of determining if a patient will be sufficiently anesthetized.

SUMMARY OF THE INVENTION

In accordance with the present invention, an EEG system and method is provided to help the anesthesiologist monitor a patient during an operation. The same, or similar, system may be used postoperatively in the recovery room and may be used to monitor patients in an Intensive Care Unit (ICU).

In the context of a surgical operation, for example, a set of four active EEG electrodes are removably fastened to the scalp of the patient. In addition, one electrode may be used as a ground and one as a reference. Measurement of the patient's brain waves preferably begins a few minutes before the anesthetic is administered. This provides data of the patient's awake state to the system.

The anesthesiologist will then administer an anesthetic, generally gas, to the patient until the patient has attained the desired plane of anesthesia, in the opinion of the anesthesiologist, based upon the patient's vital signals and other signs, including various behavioral responses and reflexes.

The patient's brain waves, at that point, are collected, analyzed and become a self-norm ("reference"). In theory, if the patient's brain waves are correctly analyzed and remain, during the operation, within a band ("reference band") close to the reference, the patient should remain at the same desired plane of anesthesia. Depending on the direction of movement of the analyzed brain waves, if outside of the reference band, either more or less anesthesia should be administered, or oxygen should be administered.

It has been found that the amount of relative brain wave power in the Theta band (3.5–7.5 Hz) is inversely proportional to cerebral blood flow and cerebral metabolism. When brain blood flow or metabolism drops, relative or absolute brain wave power in the theta band will increase, indicating that a suitable adjustment may be required. The EEG electrodes will detect increased Theta power reflecting glucose metabolic rates in brain regions near the electrodes, which are perfused by the major blood arteries to the brain, so the level of brain activity may be monitored and evaluated.

It has also been found that the brain waves from the brain stem may be analyzed to provide an indication to the anesthesiologist of the changes in the patient's ability to perceive auditory stimuli, such as speech, or to feel pain. The anesthesia prolongs transmission through the brain stem, which may be detected by measuring the latency of evoked potential (EP) components preferably a BAER (Brainstem Auditory Evoked Response) or BSER (Brainstem Somatosensory Evoked Response).

The "latency" is the time period following the presentation of a stimulus until a particular component occurs. The interval between particular successive EP (Evoked Potential) components is especially reliable as an indicator of brainstem state, for example, the interval between Peak I, arising from the arrival at the brainstem of an incoming stimulus via the auditory nerve, and Peak V, arising from arrival of that information at the inferior colliculus nucleus in the diencephalon, in normal persons older than 1 year, is approximately 4.0±0.2 milliseconds, which represents the time required for normal transmission through the brainstem.

Before the operation, the anesthesiologist will removably attach reference and ground electrodes and, for example, four EEG scalp electrodes to the patient. He/she will then administer the selected anesthesia to place the patient in the desired plane of anesthesia. At that time, measurements are made of the patient's EEG, BAER and/or BSER to provide a norm (reference or base line). Measures of vital functions such as heart rate, EKG waveshape, blood pressure, respiration and temperature may also be obtained and monitored.

In theory, the EEG system, which monitors the electrophysiology of the patient, should detect changes in the clinical state, i.e., changes in the depth of hypnosis (depth of amnesia) before there are clinical or qualitative signs of change. During the operation, the EEG system tests electrode impedances automatically and continually analyzes on-going EEG and challenges the patient with intermittent periods of stimuli to provide evoked potentials, such as BAER and BSER. These tests are automatically analyzed and the results are presented on a graphic or numerical display.

The EEG system will obtain artifact-free data samples by connecting artifact-free epochs and discarding epochs having artifacts. A selected group of features (measures at each electrode) are extracted, normalized and Z transformed to obtain Quantified EEG (QEEG). Using a database based on experience with a normal group of patients, the patient's discriminant score for the probability of awareness is calculated. The discriminant function utilizes information from those electrodes, frequency bands, and multivariate combinations of variables which are most meaningful to determine changes in the patient's state of consciousness (Patient State Index—PSI) during the operation. The PSI display warns the anesthesiologist of meaningful changes in the clinical state of the patient so that he/she may take the appropriate action to restore the patient to the selected plane of anesthesia.

BRIEF DESCRIPTION OF THE DRAWINGS

In the accompanying drawings:

FIGS. 6A and 6B are flow charts of the data analysis process, in which FIG. 6B is a continuation of FIG. 6A.

DETAILED DESCRIPTION OF THE INVENTION

I. PRE-OPERATIVE PREPARATION OF THE PATIENT

Figure 1:
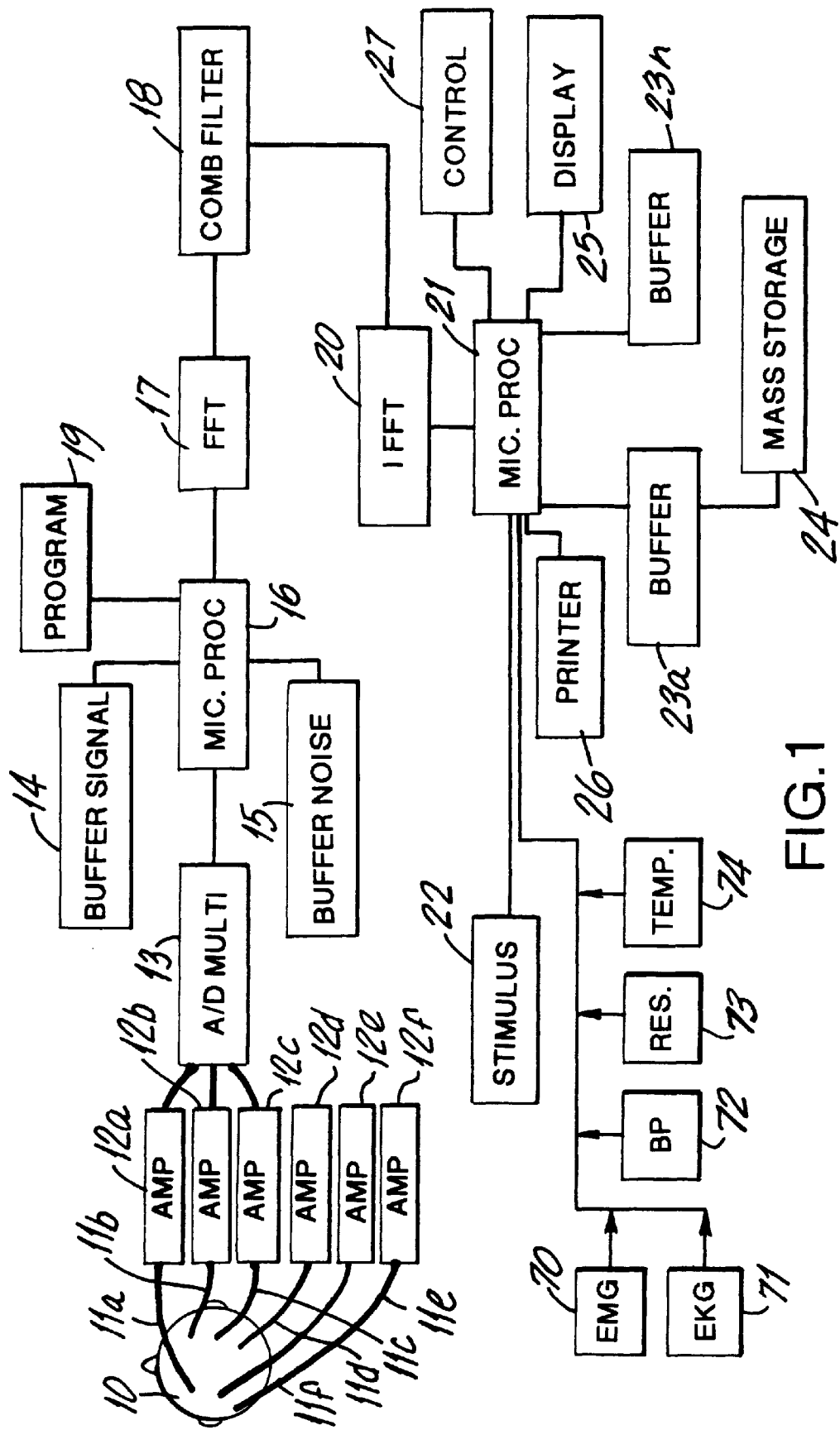
FIG. 1 is a block schematic drawing of the apparatus of the present invention.

In accordance with the present invention, the patient is prepared prior to a surgical operation. A series of EEG electrodes are removably secured to the scalp of the patient. As an example, six EEG electrodes may be used in the following locations: front left ($F_3$), front right ($F_4$), center left ($C_3$), center right ($C_4$), back left ($P_3$) and back right ($P_4$). The capital letters F,C,P refer to position location names in the International 10/20 Electrode Placement System. In addition, one reference electrode is removably positioned on the patient's earlobe or mastoid, or other suitable location, to use as a reference for monopolar recording. A conventional EKG (electrocardiogram) electrode, which may be placed on the shoulder or chest, is used as ground.

The electrodes preferably use a standard electrolyte gel for contact so that the impedances of each electrode-skin contact is below 5000 ohms. The EEG system, described below, checks the electrode-skin impedance at each electrode and displays a warning if any such impedance rises above 5000 ohms.

Preferably, but not necessarily, initial EEG measurements are taken while the patient is awake, before the anesthesia is administered.

The anesthesiologist then administers the selected anesthetics to cause the patient to attain the selected plane of anesthesia, as determined by the judgment of the anesthesiologist. That determination is made by the anesthesiologist viewing the patient's blood pressure, respiration, eye pupil dilation and other clinical signals.

A skilled EEG system operator, who may be other than the anesthesiologist, then collects a set of artifact-free EEG and BAER and BSER samples. This collection may be initiated by either having the operator push a "start" button or, alternatively, may be started automatically by the system finding the lowest depth of the patient's anesthetized state, point 201 in FIG. 7. Alternatively, data acquisition may be automatic with computer recognition and exclusion of artifacts by regression or other techniques. The baseline session contains 60 seconds of artifact-free EEG and EPs averaged using 2048 stimuli. The EEG system then subjects the data to spectral analysis using FFT (Fast Fourier Transform) and EP peak detection. Mean values and standard deviations are obtained for absolute ($uv^2$) and relative (%) power in the Delta 1 (0.5–1.5 Hz), Delta 2 (1.5–3.5 Hz), Theta (3.5–7.5 Hz), Alpha 1 (7.5–10.0 Hz), Alpha 2 (10–12.5 Hz) and Beta 1 (12.5–25 Hz) and Beta 2 (25–50 Hz) frequency bands;

proving 7 neurometric frequency bands. Other band definitions may be used. The PI-PV latency interval for the BAER (Lateral Lemniscal Transit Time), and the dorsal column nucleus (P15) to somatosensory cortex (P22) latency interval for the BSER (central conduction time—"CCT"), will be determined.

At regular intervals after this baseline is established, or upon operator demand, a statistically adequate EEG and EP sample is automatically acquired, statistically compared to the baseline, and any significant deviation detected to activate a visual or auditory alarm. Alternatively, a continuously updating sliding window can be collected, in which 2.5 second artifact-free EEG segments from current activity are added to, and the least recent 2.5 second segment removed from the set of 2.5 second segments in the window. The window may average measures across two to twenty such segments, depending upon the procedure being monitored. Similarly, average evoked potentials may be computed across, for example, 8 averages each based upon 256 samples. A continuously updated sliding window may then be computed, adding the most recent and subtracting the least recent light averages from the window.

II. THE INTER-OPERATIVE EEG SYSTEM

As shown in FIG. 1, the patient's head 10 is connected with the desired number of electrodes 11a–11f, preferably silver-silver chloride disk electrodes or less preferably needle electrodes. The drawing shows six electrodes. Should surgical conditions restrict access to some regions of the head, alternative positions may be selected.

The electrodes 11a–11f are connected to respective amplifiers, each electrode lead being connected to its own amplifier. Each amplifier 12a–12f has an input isolation switch, such as a photo-diode and LED coupler, to prevent current leakage to the patient. The amplifiers 12a–12f are high-gain low-noise amplifiers, preferably having a frequency range of 0.5 to 100 Hz, gain of 10,000 common mode rejection of 100 dB and noise of less than 1 microvolts peak-to-peak.

The amplifiers 12a–12f are connected to an analog-to-digital multiplexer 13 (A/D multiplexer). The multiplexer 13 samples the amplified analog brain waves at a rate compatible with the bandwidth of the amplifiers. The multiplexer 13 provides, at its output, sets of digital data, representing the EEG input analog signals. The multiplexer 13 is connected to "buffer signal" 14, which stores the signal, and "buffer noise" 15, which stores the noise. The buffers 14,15 are connected, and A/D multiplexer is directly connected, to the dedicated microprocessor 16. For example, the microprocessor may be an Intel 386 or Intel 486. The dedicated microprocessor 16 is connected through its dedicated 512-point FFT 17 (Fast Fourier Transform) to a series of cascading band pass filters 18 and is controlled by program 19.

The series of band pass filters is connected to a digital signal processor which takes the output from the filters and generates the Fast Fourier coefficients. The output of IFFT 20 is connected to the system microprocessor 21 (which may be Intel 386 or Intel 486) which is connected to the stimulus devices 22 (strobe goggles, loudspeaker or earphones, shock device, etc.) to the system digital storage buffers 23a–23n (only two being shown), to the mass storage 24, such as a hard disk, to the display 25, such as a CRT, and a print-out printer 26 and to the control panel 27. Preferably EP (Evoked Potential) as well as ongoing EEG is tested. When EP is used, its response may be improved using a digital comb filter 18 as described in U.S. Pat. No. 4,705,049, incorporated by reference herein. The comb filter may be considered a series of band pass and band stop filters arranged to be responsive over a selected range. The selected range is 0–1400 Hz and there are band pass filters at 10–580 Hz, 600–640 Hz and 720–800 Hz and 900–1400 Hz and band-stop filters at 0–100 Hz, 580–600 Hz, 640–720 Hz, 800–900 Hz and above 1400 Hz. The band pass filters are the "teeth" of the comb and they are selected so as to accord with the frequencies in which the signal/noise ratio is acceptable. The band-stop filters are selected to be at frequencies in which the noise is excessive. The multiplexer is programmed by programmer 24 to obtain samples of the signal and of the noise. The noise is preferably obtained when there is an absence of evoked potential stimuli and the signal is obtained during epochs up to 600 milliseconds long, beginning with presentation of the stimuli or after a pre-selected delay.

The microprocessor 21 automatically provides a timed set of stimuli from stimulator 22 which may be an audio sound from a speaker or earphone, a visual signal from a light flash, or a tactile signal from an electric shock or a vibrator. Visual flashes may be delivered using LED goggles flashing at a rate of 1/second (VEP). Auditory clicks, about 100 db 5 PL, may be delivered through a stethoscope earpiece by air conduction tubes from a magnetic speaker. 1) The rate of stimulus is preferably 7–50/second and most preferably 35–45/second, i.e., a 40 Hz auditory steady-state response (40 Hz-A55R). 2) Pairs of tone pips (for example at 1000 Hz) separated by inter-stimulus intervals of, for example, 500 ms, can be presented at inter-pair intervals of 1–5 seconds and AERs computed separately to the first and second clicks. In a randomly mixed sequence, the second tone pip is occasionally at a different pitch (for example 1500 Hz). The AER to these "unusual" or "rare" tone pips will have an exaggerated negative component at about 150 ms latency, called mismatch negativity, or MMN. The MMN or P300 can be quantified by subtracting the AER computed from the rare events scaling the integrated squared amplitude of the differences. Common clicks and rare flashes can be combined into a randomly mixed stimulus sequence, with the EP elicited by the rare stimulus providing the cognitive "event-related potential", P300 (P3). The patient's brain will respond to these stimuli providing "Evoked Potentials" (EP) which are averaged to reduce noise, providing an "Average Evoked Response" (AER). Sample size varies with stimulus mobility, ranging from 100 (VEP) to 256 for MMU or P300, to 512–2048 (BAER/BSER).

The AER is the sum of samples time-locked to the onset of the stimuli divided by the number of samples, to provide an updated average.

The program and its controlled microprocessor condition the input signals and insure that they are valid biological signals. Such validity checks on the input signals include calibration measurement, impedance measurements and automatic artifact rejection algorithms.

Figure 6A:
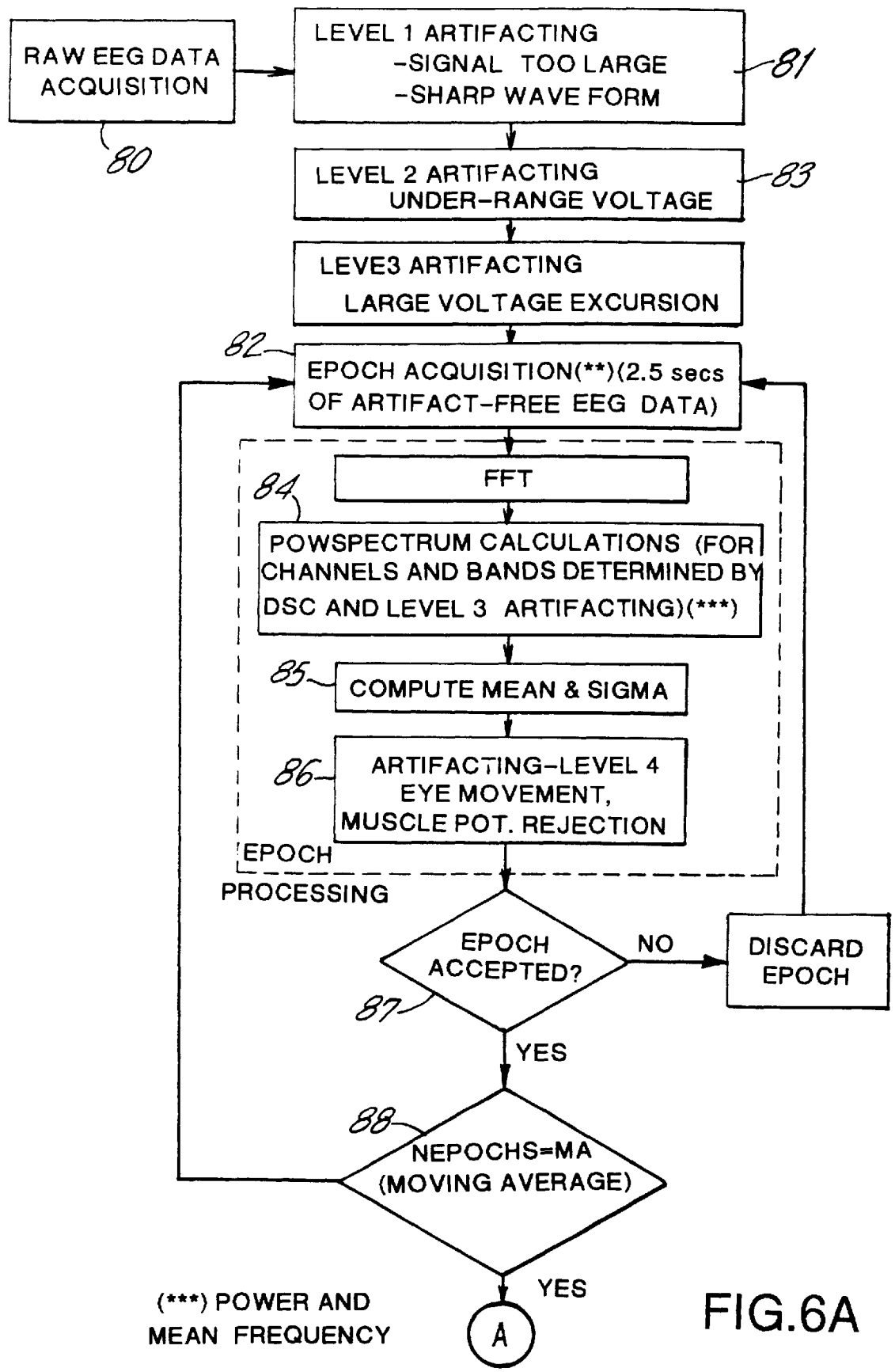
Figure 6B:
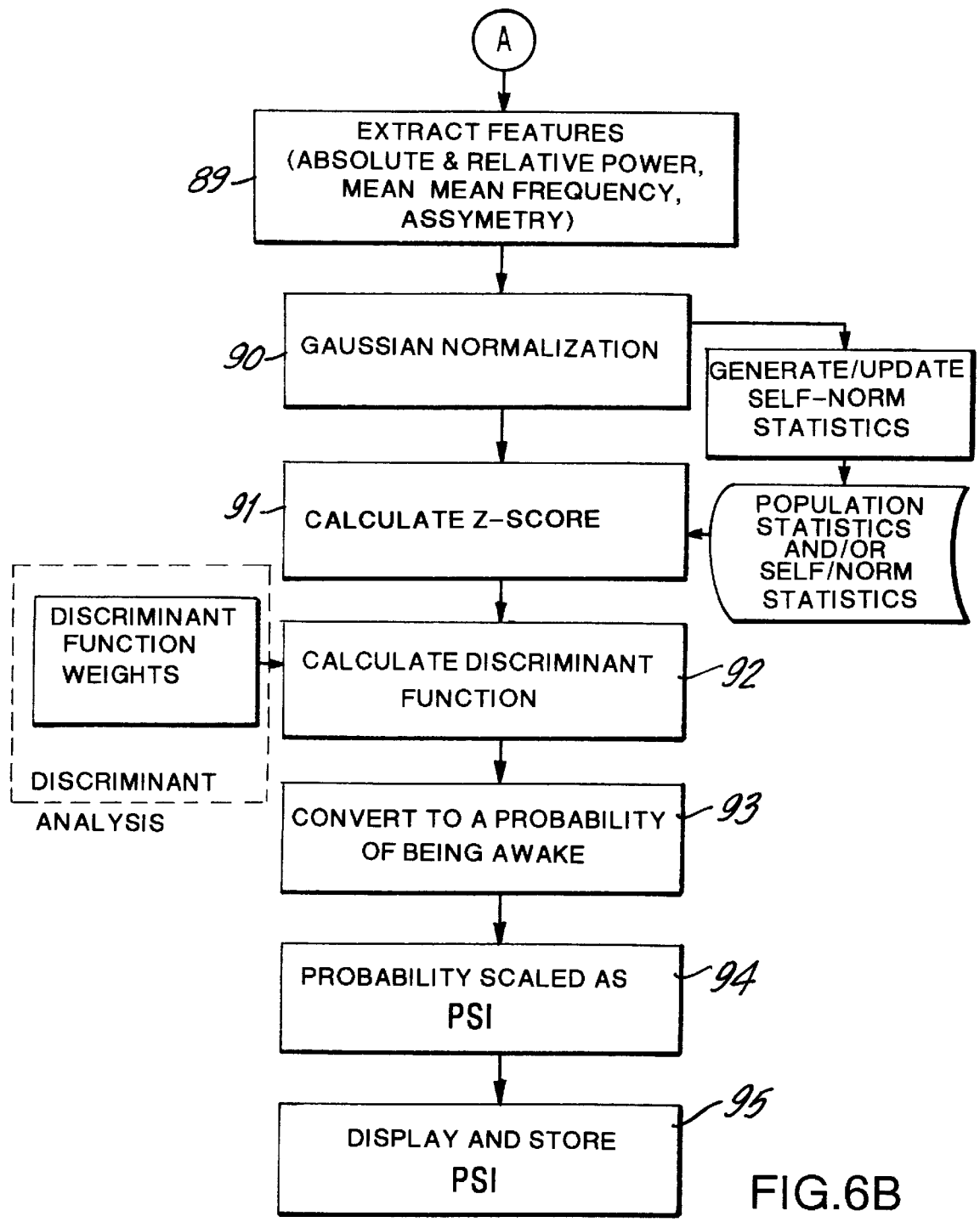

As shown in FIGS. 6A and 6B the preferred automatic artifact rejection algorithm operates on five levels. In step 80 raw EEG data, either ongoing EEG or EP, is acquired. Preferably samples are taken at the rate of 2500 per second (2500/sec.) in each channel (each electrode). The samples are filtered to eliminate noise, using band pass filters or an adaptive digital comb filter 18, if EP is being used, and samples are subjected to decimation. This provides 250 samples/sec. per channel. At steps 81 and 82, "epochs" (time periods) of artifact-free data are joined ("stitched") together. Preferably each epoch is 0.5 seconds and five "good" epochs (artifact-free) are joined to form each 2.5 second epoch. If an epoch (0.5 seconds) contains artifact it is rejected along with its preceding and succeeding epochs (0.5 seconds), i.e., 1.5 seconds are rejected. If data from one channel contains an artifact, all of the data from other channels taken during that 0.5 sec. epoch are discarded.

Level one, including step 81, determines if the electrical signal is an acceptable brain wave or an unacceptable artifact by comparison to population norms and a self-norm of the patient. At level one, if at any lead (electrode) the signal is much too large (as defined preferably by 2.5 standard deviations), the signal is considered an artifact and rejected. The rejected epoch (preferably 0.5 seconds) and its surrounding epochs are rejected—not used to form a data epoch (2.5 seconds). Simultaneously, in level 1, at step 82, epochs having sharp wave forms are found and are eliminated (not used). In each epoch the slope of the wave form (dV/dt) is calculated. If dV/dt exceeds 12 uV/ms, the entire epoch is rejected, along with its preceding and succeeding epochs. This level has a 1.5 sec. delay or time constant.

At level two, step 83, the epoch is tested for being under the preselected range of voltage, as defined preferably by 2.5 standard deviations. Generally such under-range voltage epochs are due to burst suppression. The epochs having under-range voltage are rejected, e.g., considered artifact-contaminated. However, preferably they are calculated over time and the number of such epochs or rate (number per time) are displayed to the user. This level has a time constant of 0.5 seconds.

At level three, those epochs are rejected having any waves having a point which is a large voltage excursion. Preferably, the RMS (Root Mean Square) of the voltage is calculated across a sub-epoch, for example, over 0.25 seconds (250 m secs), which is added to a moving window of 8 seconds. If any point exceeds the RMS of the moving window by a predetermined amount, i.e., 4 S.D., the entire sub-epoch (interval of 250 m secs) is rejected. This level has a time constant of 4 sec., totalling 6 seconds for all 3 levels.

If an epoch is found acceptable at levels 1–3 it is then subjected to FFT (Fast Fourier Transform) for the level 4 test. This is done by a digital signal processor connected to the output of the band filters. If the epochs FFT ($\Delta$) is too large it is rejected. For example, it is rejected if it exceeds 2.5 S.D. of a baseline sample. In addition, the rate (epochs per time period) of such excessive FFT epochs is displayed.

In regard to population norms, the wide band of acceptance, i.e., ±2.5 S.D. (Standard Deviation), means that even patients with abnormal brain wave signals, such as physically healthy psychotics, generate a sufficient proportion of acceptable sample epochs.

At level four, artifact rejection of step 86 is obtained directly from leads (electrodes) which detect muscle activity and other artifact. Preferably a lead is placed close to the eye to detect head movement, eye blink, and eye movement, and other leads may be placed at suitable muscle locations (EMG). These leads are connected to an electromyograph (EMG) amplifier. When they detect muscle activity, the epoch (in 0.5 seconds) containing the muscle activity (defined as 2.55 S.D. above a normal baseline), and its surrounding epochs, are rejected.

In addition, there is a display to the user of the EMG rate (percent of excessive EMG per time period). If an epoch passes the test at all four levels it is accepted as being artifact-free data and joined (stitched) to form a 2.5 second epoch. As shown in FIG. 6A, an N (number) of epochs (2.5 secs) are averaged to obtain an MA (Moving Average), in step 88. Preferably the Moving Average is an average of 20 epochs, each of 2.5 seconds.

The next step (FIG. 6B) is to extract features. The features are normalized in step 90, preferably using Gaussian normalization by log transformation, and Z scores are calculated (step 91). The steps 85–89 are discussed in detail in a subsequent section.

The preferred list of measures (features) extracted by FFT is as follows: For each of the electrodes; 7 bands of absolute power (total T1, Delta 1, Delta 2, Theta, Alpha 1, Alpha 2, Beta 1, Beta 2), 7 bands of relative power (Delta 1, Delta 2, Theta, Alpha 1, Alpha 2, Beta 1, Beta 2) for the three pairs of homologous electrodes; coherence of the total EEG and each frequency band. An overall multivariate measure of deviation, such as a Malanobis distance, is computed for each lead and across selected combinations of leads.

In addition, using four electrodes, the variables selected by step wise discriminant utilize GRADIENTS, which are combinations from anterior to posterior, i.e., Fpz—Fz, Fpz—Cz, Fpz—Pz, Fz—Cz, etc.

III. INTRA-OPERATIVE PATIENT MONITORING

During the surgical operation, the patient is kept on the EEG system of FIG. 1, or re-connected to the system if for some reason there is an interruption.

The objective of the EEG monitoring is to provide the anesthesiologist with sufficient information regarding the state of the patient's brain to maintain the patient at the selected plane of anesthesia.

In general, this involves the concurrent or alternating collection of periodic artifact-free on-going EEG sessions, and evoked potential challenges, such as BAER/BSER, throughout the operation, the realtime analysis of the data and updated comparisons of features extracted from that data to a normative database constructed from a population of surgical patients sedated but awake prior to induction of anesthesia, the pre-induction but sedated state of the patient and the patient's baseline after induction of anesthesia ("self-norm").

In addition to the collection and analysis of on-going EEG, discussed above, the patient is automatically subjected to suitable stimuli at selected intervals over the course of the operation to provide sets of EPs (Evoked Potentials).

The brain stem auditory evoked response (BAER) has, in normal subjects, 5 peaks. These latencies are expressed as milliseconds from the stimuli and are closely similar in shape and latency across neurologically normal persons. The time shift of certain of these latencies, and their suppression, is indicative of the patient's response to anesthesia. The first 5 positive peaks, in response to click (auditory) stimulus, are believed to reflect the successive activation of the acoustic nerve, cochlear nucleus, superior olivary complex, lateral lemniscus and inferior colliculus. The Peak I–Peak V latency interval is probably the preferred BAER indicator to use.

Another useful indication of the patient's state is the brain stem somatosensory evoked response (BSER). It is believed that the successive peak latencies reflect, in order, the activation of the dorsal column nuclei, medial lemniscus, thalamus, sensory radiation and the first cortical synapses. The P15–P22 (dorsal column nucleus to cortex) latency interval (CCT) is probably the preferred indicator to use.

The feature extraction method for VEPs, MMN, or P300 involves alternative ways to describe EP signal strength, variability, and interhemispheric symmetry. These features are extracted for latency domains: 80–200 and 200–500 msec. Measures of signal strength ("features") include absolute peak-to-peak (p—p) amplitude and "normalized" p—p amplitude. Normalized p—p amplitude is obtained by defining the largest amplitude as 100%, and other measurements are scaled relative to that maximum. Measures of EP variability include the standard deviation of the p—p amplitude (s), the variance ($s^2$), and log variance ($\log s^2$). The standard deviation of the p—p amplitude (s) is an rms measure: $rms=(s_{Pmax})^2+(s_{Pmin})^2$, where s is the standard deviation, and $_{Pmax}$ and $_{Pmin}$ are the largest positive and largest negative peaks, respectively, within a particular latency domain (100–250 msec or 250–500 msec). $\log s^2$ is computed because $s^2$ itself is not normally distributed. A measure of signal-to-noise ratio (S/N) is computed as well, where "signal" is the p-p amplitude, and "noise" is its standard deviation. The principal measure of bilateral EP symmetry is the Pearson product-moment correlation (r) across the time bins, computed for EPs recorded from homologous derivations in left and right hemispheres ($C_3$ vs. $C_4$, $F_3$ vs. $F_4$ and $P_3$ vs. $P_4$, etc.), and referred to as "interhemispheric coherence". The square of the product-moment correlation coefficient ($r^2$) is also obtained for each homologous pair of derivations. Across the set of six electrodes, there are thus 91 quantitative EEG descriptions, 194 VEP and P300 descriptors, and two preferred brainstem EP descriptors.

All of these various features are then compared against the "baseline" (data collected from the pre-operative patient after being anesthetized). As experience with anesthetic effects is accumulated, it can be expected that this large set of features will be decreased. Each measure may be z-transformed using the corresponding mean and standard deviation obtained from the baseline. Each z-score for a patient is calculated in the following manner: the reference pre-operative mean, X, for a particular measure, is subtracted from the value X for that measure obtained from the patient during the operation. The difference, X–X, is divided by the standard deviation, s, of that measure for the baseline. Thus, $z=(X-X)/s$. If the distribution of a variable is Gaussian, the z-score provides an estimate of the probability that an observed measure is "abnormal" i.e., improbable., for that patient.

In addition, the patient's measures are statistically compared with a normative reference database based on measures obtained inter-operatively from a group of normal patients of the same age having successful outcomes of specific surgical procedures using specific anesthetic materials. For example, a database is obtained on the surgical procedure of a prostate operation in a normal group of patients of the same age using the gas halothane. Further, the patient's measures are statistically compared to a normative reference database based on measures taken from a normal group having post-operative reports of successful operative administration of anesthesia, regardless of the operative procedure.

The preferred method and system to compare the patient's EEG and EP measures with a normative reference data base is to use "discriminate functions". As mentioned above the Z-scores are obtained for each feature, i.e., each EP resulting from one stimulus at one electrode. These Z-scores are then used to distinguish between conditions (states) of anesthesia, for example, as follows:

(a) fully anesthetized—the patient's movements are blocked, the patient feels no pain and is not aware of the operation.

This is the desired condition.

(b) partially anesthetized - the patient's movements are not fully blocked or the patient feels some pain or the patient is at least partly aware of the operation. This condition is generally satisfactory.

(c) unanesthetized—the patient's movements are not blocked; the patient feels pain and is aware of the operation.

These conditions, or similar condition categories, of a patient during an operation, may be distinguished through discriminant analysis using discriminant functions. Such functions are composed of weighted combinations of subsets of variables, the subsets being Z scores. Each of the subsets (each Z score) is selected, on the basis of experience and experimentation, because it significantly contributes to the discrimination, i.e., discrimination between fully anesthetized and partially anesthetized. The weighting of the subsets (how much should each Z score contribute toward the discrimination) is also based on experience and experimentation.

For example, using 7 frequency bands and 6 electrodes to derive ongoing EEG provides a large number of potentially sensitive measures. However, using stepwise discriminant functions it may be determined, for a particular operation and anesthetic, that only 3 or 4 of those features are especially meaningful.

A preferred way of calculation, using the computer system, to automatically determine if a patient is awake (state A) or unconscious (state B), after being anesthetized, is as follows:

Each weighting of a subset designated $w_1, w_2, w_3 \ldots w_j$ and $w_1', w_2', w_3 \ldots w_j'$ is based on experience and experimentation, as mentioned above. The scores A and B are the combined weightings and Z scores, namely:

$$A = w_1 Zscore_1 + w_2 Zscore_2 \ldots w_j Zscore_j$$
$$B = w_1' Zscore_1 + w_2' Zscore_2 \ldots w_j' Zscore_j$$

The probability of the patient being awake is:

$$\frac{EA}{E_A + E_B} \times 100$$

The probability of the patient being unconscious is:

$$\frac{EB}{E_A + E_B} \times 100$$

These two probabilities are compared. If the probability that the patient is awake exceeds, with a determined guardband (extent) the probability that the patient is unconscious, then an alarm is generated by the system.

The distributions of features of two groups of subjects (where the groups belong to different diagnostic categories) can be thought of as two clouds of points in a multidimensional space in which each dimension corresponds to a feature. In this case each feature is a Z score and the diagnostic categories are the degrees of anesthezation. There may be no significant differences between two groups (i.e., between fully and partially anesthetized) in some dimensions (i.e., in some features) but there may be significant differences in other dimensions. A problem arises when these clouds of points overlap (i.e., when there is no apparent significant difference between the two groups with respect to some features). One attempts to define a boundary through the clouds of points to create a first zone which includes as much as practicable of the first group and as little as possible of the second group, and a second zone which includes as much as practicable of the second group and as little as practicable of the first group. A third zone is defined to encompass an overlap region where no reliable classification can be made In principle, a discriminant function weights the values of selected features for a new individual and adds these weighted values to specify a single point as the relevant multidimensional space. This single point then would be in one of the three zones, and the individual would be classified accordingly.

A use of discriminant analysis in QEEG is found in U.S. Pat. No. 5,083,571 relating to psychiatric classification of individuals, incorporated by reference. The present use of discriminant functions is not to classify a group into a class or an individual with respect to specific disorders (psychiatric diagnosis); but rather to characterize the brain state of a patient at a particular time (intraoperatively).

For this purpose it is preferred that the discriminant analysis be performed, during the operation, using Z scores based on self-norms (the same patient pre- or post-induction) and population samples (normal patients of the same age during similar operations using the same anesthetic or across anesthetics).

A probabilistic classification of the anesthetized state of a patient can be determined using discriminant functions derived from stepwise discriminant analysis of the same patient prior to the operation or/and normal test populations. Each discrimination is based on n functions where n is equal to the number of groups in that discrimination. The functions are defined as a sum of selected Neurometric variables, each multiplied by a coefficient to yield a discriminant score. The selection of the variables and the weightings of the coefficients are matters of experience and experimentation. Generally, each variable is a Z score. The result of each function is a single discriminant score $s_i$. A classification probability $P_i$ that a patient's state belongs to group i; where i is for example fully, partially or not anesthetized, is calculated according to the following formula:

$$P_i = \frac{\exp(s_i)}{\sum_{i=1}^{n} \exp(s_i)}$$

The group (state, i.e., fully anesthetized) for which a patient has the highest probability $P_i$ is selected as a potential classification group (state).

This probability $P_i$ is then compared to a guardband cutoff levels for this group $a_i, a'_i, a''_i, \ldots$, where $a_i < a'_i, a''_i, \ldots$ which correspond to classification errors $\epsilon_i, \epsilon_i'$, and $\epsilon_i''$, where $\epsilon_i < \epsilon_i'$, $< \epsilon_i''$. For example, $\epsilon_i = 10\%$, $\epsilon_i' = 5\%$, and $\epsilon_i'' = 2.5\%$.

If $P_i < a_i$ then the patient is not classified. If $a_i \leq P_i$ $a'_i$ then the patient is classified in group i, with confidences 1-$\epsilon_i$. If $a'_i \leq P_i < a_i \Delta$ then the patient is classified in group i, with confidence 1-$\epsilon_i'$. If $a_i \Delta \leq P_i$ then the individual is classified in group i, with confidence 1-$\epsilon_i \Delta$.

Alternatively, measures may be assessed by computing sensitive indices such as $$\frac{\text{delta plus theta}}{\text{alpha plus beta}} \text{ or } \frac{\text{theta}}{\text{alpha}}$$

and calculating the ratio of such combined variables or of univariate measures or composite variables extracted from successive samples of EEG/EP relative to baseline values. Another alternative to the Z-transform is to use the F-ratio derived from the variance within the samples divided by the variance of the baseline. Statistically significant thresholds can be defined for each of these alternatives.

The preferred way of displaying, to the operating anesthesiologist, as an example, that there may be a problem with the amount of anesthetic being delivered to the patient, is the Patient State Index (PSI). The PSI is a number which is displayed on a monitor. For example, using a scale of 100, the patient would be receiving a satisfactory amount of anesthetic if the PSI is between 40–60; an excessive amount if the PSI were below 40 and an insufficient amount if the PSI were above 60. These set points would be defined as a result of clinical trials. The PSI is obtained by calculation of the patient's discriminant functions (step 92—FIG. 6B). The discriminant scores are converted to a probability of being awake, i.e., probability of tending to arousal.

That probability, in step 94, is scaled as the PSI. Preferably such scaling uses decimation (1 in 10 selection) and a low-pass filter to reduce noise. In step 95, the PSI is displayed on display 25 (on the monitor) and stored in system storage (mass storage 24). The PSI is generated by averaging the current data with a previous 10 sec. epoch to arrive at a current PSI. Thus, the time constant for the entire system is 7.5 seconds.

Figure 2A:
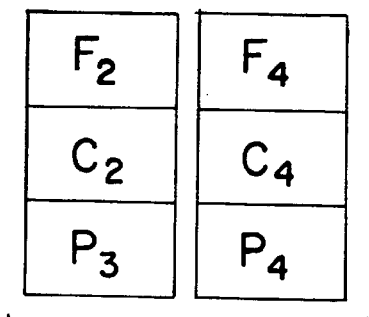
FIG. 2A is a diagram of one display showing the corresponding position in the display for each electrode.

Alternative to the Patient State Index display, the EEG system may combine measures, after having Z-transformed them relative to the baseline, and display the combinations as "trajectories". Upper and lower alarm limits can be separately adjusted. The screen, as shown in FIG. 2A, will show six trajectories (vectors) corresponding in location to the six EEG electrodes, plus one trajectory for every EP category. It is conceivable that, in view of future knowledge about such monitoring, selected measures may be used to achieve feedback control of anesthetics.

Figure 7:
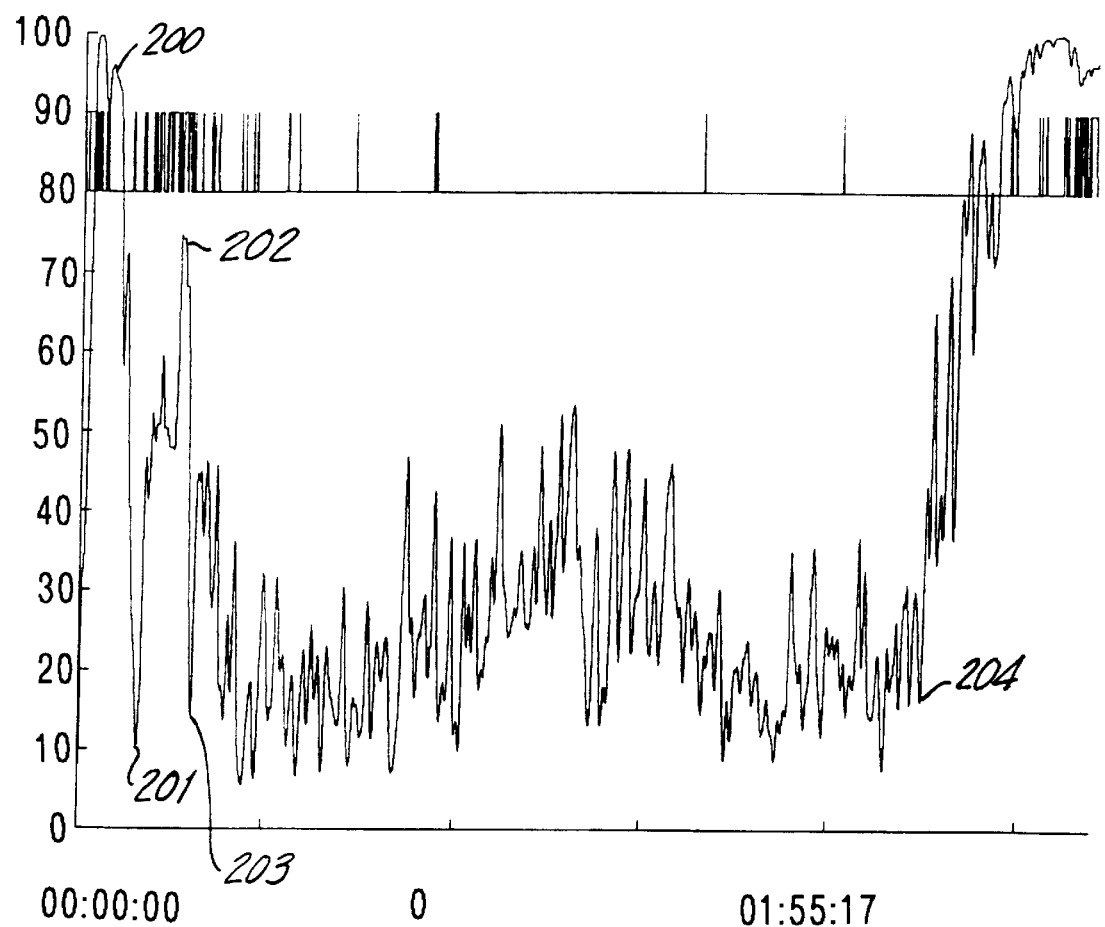
FIG. 7 is a chart of a patient's Patient State Index (PSI).

FIG. 7 is a chart showing a patient's PSI. The Y axis is arbitrary units 0 to 100 and the X axis is time. The patient is awake, before anesthesia is administered, at point 200. Then anesthesia is given and he is fully anesthetized, before the operation, at point 201. There is a rebound effect at point 202 and then the PSI, at point 203, shows that the patient is anesthetized. The operation is over and the patient awakes, starting at point 204. The operation occurs in the period between points 203 and 204.

Figure 4:
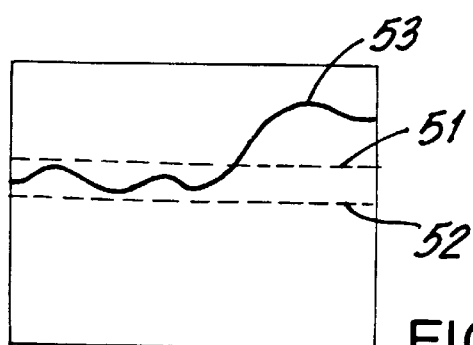
FIG. 4 is a display of a trajectory of the patient's state as measured at one electrode.

As shown in FIG. 4, which is an enlargement of one of the six scales of FIG. 2A, the baseline is defined as a mean 50. The upper and lower confidence intervals of 2.5 standard deviations from the mean are shown as lines 51 and 52. Any excursion of the trajectory 53 beyond the normal band, defined by lines 51 and 52, is "abnormal" and will trigger a warning signal, such as a flashing light or buzzer or a vibratory signal on a wrist band worn by the operator.

Figure 2B:
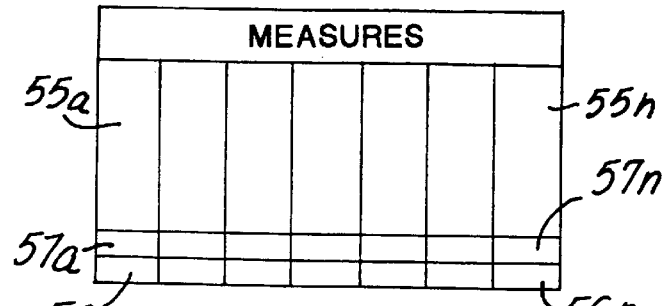
FIG. 2B is a display of the measures at one electrode.

An alternative display is shown in FIG. 2B, which shows a moving chart (histogram) type of display. That display will be shown individually for each of the 6 electrodes, either on the same screen or in sequence. Each measure (feature) has its own column 55a–55n. The latest result of each measure is color coded, preferably using a "heat" color scale, and shown as a bar 56a–56n on the bottom of each column. The prior measure result is moved upward (scrolled up) and becomes the bar 57a–57n. In this way changes in each measure, at each electrode, may be displayed. The bars will change (scroll upward) with every update of the assessment, at intervals which will depend upon data variance, the full set of data being monitored, and ambient electrical noise levels and may range from 5 to 120 seconds for different EEG and EP measures.

In addition to the EEG electrodes an EMG (electromyograph) electrode 70 may be used at a frontal scalp location. The EEG electrodes at the front of the scalp, when they detect energy in the Beta 2 band (25–50 Hz) are detecting facial muscle activity and are acting as an EMG electrode. The operator can determine, in order to arrive at a proper plane of anesthesia, using the frontal electrodes in the Beta 2 band or/and the EMG electrode 70 if there is too much muscle activity (indicating insufficient anesthesia).

The system compares a first set of data from the patient before anesthesia is administered and a second set of data after the plane of anesthesia is attained, but before the operation. In addition, the system compares a first set of data from the patient, obtained after the plane of anesthesia is attained with a second set of data obtained during the operation. In each case the first and second sets of data consist of data from the EMG electrode 70 and/or frontal EEG electrodes. In each case the system automatically compares the two sets of data and provides a warning if the comparison indicates a significant (±2.5 SD) deviation. The two cases are (i) a comparison of pre-anesthetized v. anesthetized and pre-operation and (ii) anesthetized and pre-operation v. anesthetized and during the operation.

Each patient may be also connected to a set of EKG (electrocardiogram) electrodes and amplifier 71 to detect changes in EKG waveshape and rate of heart activity, particularly the R—R interval and its variance. Preferably both the mean R—R interval and $6_{R-R}$ are calculated. A significant, for example, 2.5 SD, decrease in R—R interval (tachycardia) may indicate inadequate analgesia resulting in autonomic responses (heart rate response) to painful stimuli. The variance of the R—R interval decreases with increasing depth of hypnosis.

The patient may be also connected to a blood pressure detector 72 (sphygmomanometer) to measure systolic, diastolic and pulse pressure and may be connected to sensors for respiration, expired $CO^2/O_2$ and body temperature. The EKG amplifier 71 and the EMG electrode amplifier 70 and blood pressure device 72 (BP) respiration (RES) 73 and temperature (TEMP) 74 sensors are connected to the microprocessor 21 and may be of conventional construction. A significant, for example, 2.5 SD, increase in blood pressure, detected by BP 72, may indicate inadequate analgesia. If the patient is not artificially ventilated, a more rapid respiration, detected by RES 73, may also indicate inadequate analgesia. A sustained, and significant (2.5 SD), increase in body temperature may indicate malignant hyperthermia, which requires immediate clinical intervention.

In each of these cases, of R—R interval, blood pressure and respiration, the patient's data is collected by analog sensors, amplified and converted to digital data. In each case, a first set of data is collected as a self-norm after the patient is anesthetized and pre-operation and a second set of data is collected post-anesthetized and intra-operation, the two sets compared and a warning is generated should a significant (2.5 SD) deviation from the self-norm occur. The anesthesiologist, in response to the warning, will increase, or decrease, the amount of anesthesia being administered.

The system also detects if there is low mean total EEG power (EEG power drops significantly below its mean value) simultaneously in all EEG electrode leads. Such low total EEG power arises from burst suppression, indicating too much anesthesia. The operator is warned if there is too much facial muscle activity (too little anesthesia) or if there is burst suppression (too much anesthesia). If warned of burst suppression, the operator should decrease the amount of anesthesia being administered to the patient. The system compares data for total EEG power from all EEG electrodes as performed in detecting facial muscle activity, namely, comparisons of first and second data sets as between (i) pre-anesthetized v. anesthetized and pre-operation and (ii) anesthetized and pre-operation v. anesthetized during the operation.

Along with displaying the PSI in graphical or numeric form to the operating anesthesiologist, it is preferred to also display, in graphical or/and numerical form, the data quality, suppression and EMG. The data quality graph would indicate how much data is being removed due to artifacts. For example, too much data being discarded could indicate a loosely attached electrode or loose connection and would alert the operator to check the connections. Preferably data quality, EMG and suppression are constantly displayed on the monitor as bar graphs.

It has been reported that generally patients, even during an operation, have an increase in heart rate (R—R interval) with the inhalation of breath. The heart rate normally decreases with exhaling of breath. The ratio of those two heart rates is called RMSA (Respiratory Mean Sinus Arrhythmia). It is a vector which changes (becomes disoriented) depending on the depth of the patient's anesthetized state. The system measures the breath rate of inhalation and exhalation of breath (respiration) and the heart rate (R—R interval). It then compares these rates, as in the prior embodiments, of the patient, before being anesthetized, with the rates after being anesthetized (pre-operative) and during the operation. These comparisons provide additional information which is displayed to the anesthesiologist and provides a warning signal if the patient's depth of anesthesia increases or decreases beyond a guard-band.

IV. THE RECOVERY ROOM/ICU EEG SYSTEM

Figure 3:
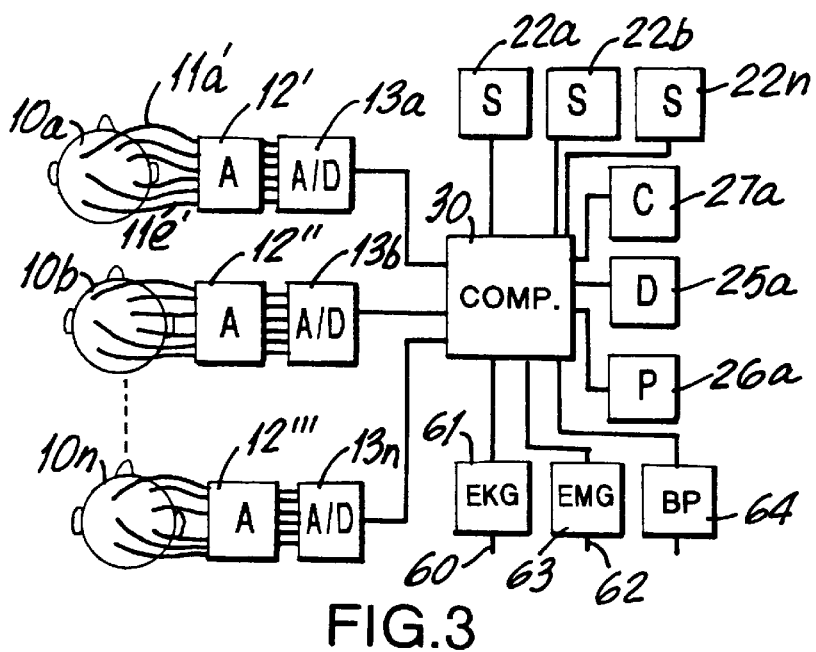
FIG. 3 is a block schematic drawing of another embodiment of the apparatus of the present invention.

As shown in FIG. 3, a multi-patient monitoring system is used in the recovery room and the intensive care unit (ICU). It consists of six electrodes 11a'11e' removably connected to the head 10a–10n of each patient, i.e., 24 electrodes for a 4-patient system. As in the embodiment of FIG. 1, each electrode is connected to an amplifier (the group of 6 amplifiers shown as 12'14 12''') and the amplifiers connected to an analog-to-digital multiplexer 13a–13n. The computer 30 includes the buffer signal, buffer noise, dedicated microprocessor, FFT, digital comb filter, IFFT, system microprocessor, stimulus device control for a stimulus device 31a–31n for each patient, storage buffers and mass storage as in the FIG. 1 apparatus. The computer 30 is connected to control panel 27a and the computer is connected to and controls display 25 and printer 26a. In the embodiment of FIG. 3, the "raw" digital data from each patient is transmitted to central computer 30. Alternatively, each patient station may have an "on-board" computer, so that only the changes in the patient's state would be transmitted to the central computer 30.

A nurse or doctor is able to monitor a number of patients by watching a single windowed display, for example, on a video monitor. For example, each minute the trajectory from a different patient, in order, might be displayed, or a different critical measure from the patients in each bed might be updated on their trajectories.

Each patient is also connected to a set of EKG (electrocardiogram) electrodes 60 to detect changes in EKG waveshape and rate of heart activity and to EMG (electromyograph) electrodes 62 to detect muscle activity, to a blood pressure detector 64 (sphygmomanometer) to measure systolic, diastolic and pulse pressure, to sensors or respiration, expired $CO^2/O_2$ and body temperature. The EKG amplifier 61 and the EMG amplifier 63 and blood pressure device 64, respiration and temperature sensors, are connected to the computer system 30 and may be of conventional construction. These measures are similarly updated on vital sign trajectories.

In the recovery room or ICU, the doctor will monitor the patient and obtain a new self-norm for the patient at each stage of recovery. For example, in the recovery room as the muscle paralysis is lessened and the patient starts to become conscious a new self-norm is obtained. If the patient then regresses, the new self-norm will provide the statistical basis for the warning signal of the regression. Trajectories can be plotted against individual self-norms for most sensitive detection of clinically significant fluctuations within each patient, against population norms to assess deviation from normal healthy persons, or against group average values constructed against some reference group of patients (e.g., "good" versus "bad" outcomes). Note that diurnal rhythms related to sleep cycles may require time-dependent changes in threshold definitions for alarms, e.g., theta power increases with drowsiness.

In the ICU the data from bedside amplifiers attached to all the monitored patients are transmitted to the nursing workstation, which includes multiplexed analysis capabilities in the computer 30 and display 25a. Regularly updating trajectories with alarms help nursing staff monitor each patient. When significant change occurs, a new set of data becomes the patient's current self-norm.

Figure 5:
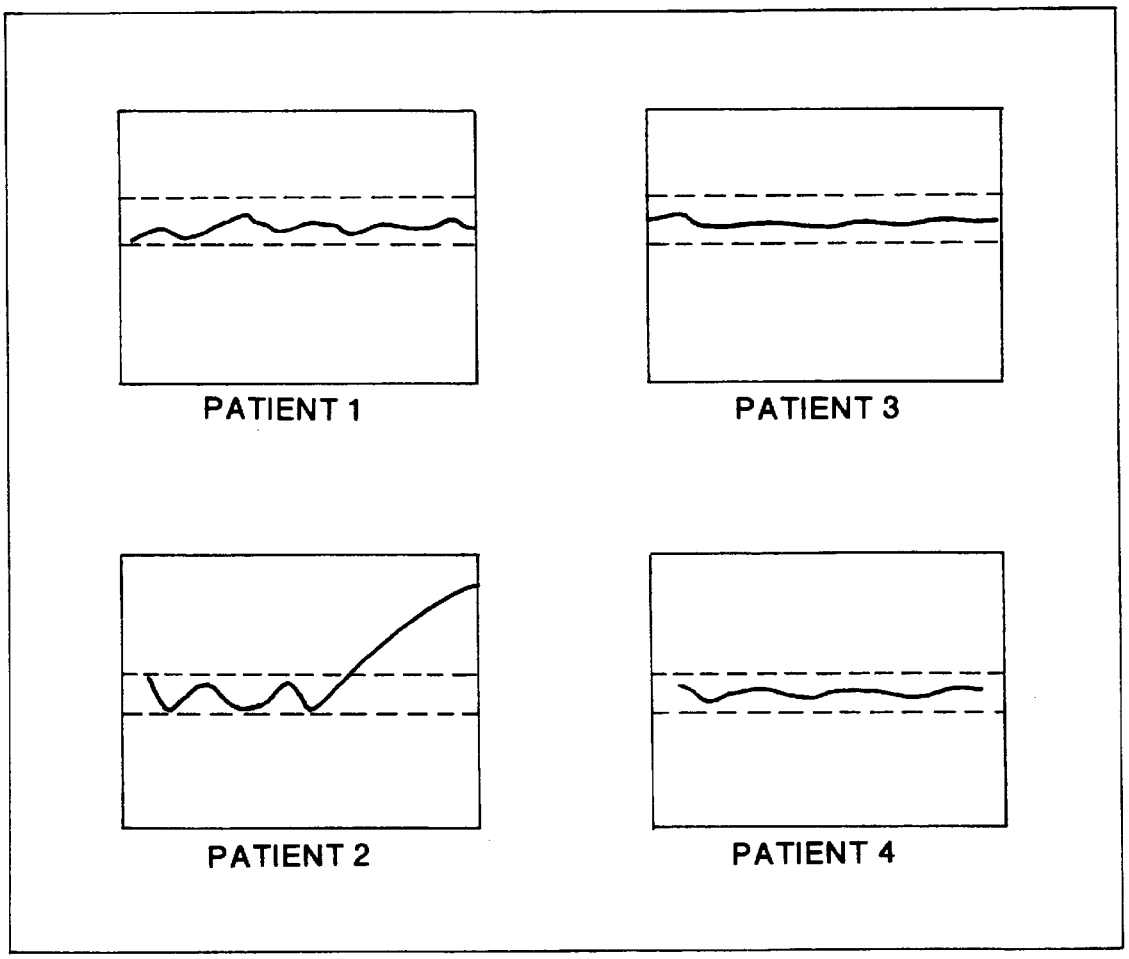
FIG. 5 is an illustration of a display for the system of FIG. 3.

The information from the EEG may be combined with the EKG and other vital sign data to provide a multi-variate overall state measure. If any constituent measure or the overall state becomes abnormal, for example, more than 2.5 or 3 standard deviations from the mean, then the alarm warning is sounded. The multi-variate measure, as shown in FIG. 5, is shown as a trajectory between the normal lines 61 and 62 for each patient, on the screen of the display 25a. This composite, or univariate trajectories, may be printed out, on a regular basis, by printer 26a. Preferably, the display 25a is a multi-window display on a video monitor in which the state of each patient is simultaneously shown in a window of the display.

Other embodiments are within the scope of the claims. For example, in the embodiment described above, the anesthesiologist uses his own judgment to select the proper plane of anesthesia. Early in the use of the present invention this, indeed, will be the case. However, after a database has been established, which comprises both the data from the operation and subsequent patient outcomes, the monitoring system of the present invention may play a greater role in suggesting the proper level of anesthesia. Alternatively, because various anesthesiologists may differ in their preference of anesthetics or level of anesthesia, an additional database which stores only the cases from one anesthesiologist may be relied upon. One method by which the monitor may suggest the proper level is to create a ratio which compares the pre-anesthesia baseline to the present level of anesthesia utilizing a variable such as PI-PV, the latency of P300, or other EP component. Ratios based on BSER or BSSER, or other such physiological measures or frequency distribution of the EEG or other type of statistical analysis of these measures may also be used. This ratio might be termed a c/u ratio (consciousness/unconsciousness ratio) rather than "consciousness meter" because the latter term suggests that one can say something about levels of consciousness based on this ratio which has not been proven scientifically.

What is claimed is:

1. An electroencephalograph (EEG) method for monitoring the plane of anesthesia of a patient undergoing a medical procedure, comprising:

(a) removably connecting a set of EEG electrodes to the scalp of the patient and administering sufficient anesthesia to the patient for the patient to attain the plane of anesthesia selected by the anesthesiologist;

(b) presenting a set of stimuli to the patient and amplifying and digitizing the brain wave evoked responses to the stimuli and the patient's ongoing brain wave activity collected from the EEG electrodes to provide a first set of digital data representing a set of features of the patient's brain waves in the patient's pre-operative anesthetized state and recording the first set of digital data in computer system memory;

(c) during the operation, presenting the same set of stimuli to the patient and amplifying and digitizing the brain wave responses to the stimuli and the patient's on-going brain wave activity to provide a second set of digital data regarding the same set of features as the first set;

(d) using the computer system to statistically compare the first and second sets of digital data on a feature-by-feature basis;

(e) deriving a discriminant score based on the comparisons of (d) by selectively weighting, selecting and combining a number of said feature-by-feature comparisons;

(f) combining the discriminant scores to derive probabilities that the patient is in a specific anesthetized state;

(g) applying selected guardbands (rule-out levels) to the probabilities to classify the anesthetized state of the patient on the basis of the probabilities; and (h) providing a warning if the patient is not in a fully anesthetized state during the operation based on the classification of (g); and (i) adjusting the anesthesia administered to the patient during the operation in response to the warning to restore the patient to the selected plane of anesthesia.

2. The method of claim 1 and including statistically comparing the second set of data with a normative reference database of features based on the successful outcomes of specific surgical procedures using specific anesthetic materials and deriving a second discriminant score based thereon.

3. The method of claim 2 in which the normative reference database of features are in the form of age-corrected Z-scores which are in the same dimensional unit.

4. The method of claim 1 and including statistically comparing the second set of data with a normative reference database based on post-operative reports of successful operative administration of anesthesia.

5. The method of claim 1 wherein the stimuli are auditory and the evoked responses are brain stem auditory responses (BSAR).

6. The method of claim 1 wherein the stimuli are sensory and the evoked responses are brainstem somatosensory evoked responses (BSER).

7. The method of claim 1 wherein a plurality of EEG electrodes are employed and the comparisons of (d) are displayed in a display corresponding to the locations of the EEG electrodes and displaying graphic trajectories representing changes in brain wave states at each EEG electrode.

8. The method of claim 1 wherein the measures of the ongoing EEG include absolute and relative power in the Delta, Theta, Alpha and Beta bands.

9. The method of claim 1 wherein the warning is a visual signal on a computer system monitor screen, a sound or a vibratory signal on a wrist band worn by the operator.

10. The method of claim 1 wherein the patient's ongoing brain wave activity in (b) and (c) includes the relative brain wave power in the Theta band (3.5–7.5) as an indication of cerebral blood flow.

11. An electroencephalograph (EEG) method for monitoring the plane of anesthesia of a patient undergoing a medical procedure to determine the patient's ability to feel pain, comprising:

(a) removably connecting a set of EEG electrodes to the scalp of the patient and administering sufficient anesthesia to the patient for the patient to attain the plane of anesthesia selected by the anesthesiologist;

(b) presenting a set of stimuli to the patient and amplifying and digitizing the brain wave evoked responses to the stimuli collected from the EEG electrodes to provide a first set of digital data representing a set of features of the patient's brain waves in the patient's pre-operative anesthetized state and recording the first set of digital data in computer system memory;

(c) during the operation, presenting the same set of stimuli to the patient and amplifying and digitizing the brain wave responses to the stimuli to provide a second set of digital data representing the same features;

(d) using the computer system to statistically compare the first and second sets of digital data including comparison features representing prolongations of the latency of periods of the brain stem and (e) providing a warning if any latency periods are abnormal by being of a period shorter than a selected range and if the patient is classified in (g) in a non-fully anesthetized state;

(f) providing a discriminate score based on the comparisons of (d) by selectively weighting, selecting and combining a number of the feature-by-feature comparisons;

(g) combining the discriminant scores to derive probabilities that the patient is in a specific anesthesized state;

(h) applying selected guardbands (rule-out levels) to the probabilities to classify the anesthetized state of the patient on the basis of the probabilities;

(i) providing a warning if the patient is not in a fully anesthetized state during the operation based on the classification of (h); and (j) adjusting the anesthesia administered to the patient during the operation in response to the warning to restore the patient to the selected plane of anesthesia.

12. The method of claim 11 and including statistically comparing the second set of data with a normative reference database based on the successful outcomes of specific surgical procedures using specific anesthetic materials.

13. The method of claim 11 and including statistically comparing the second set of data with a normative reference database based on post-operative reports of the successful operative administration of anesthesia.

14. The method of claim 11 wherein the stimuli are auditory and the evoked responses are brain stem auditory responses (BSAR).

15. The method of claim 11 wherein the stimuli are electrical or tactile and the evoked responses are brainstem somatosensory evoked responses (BSER).

16. The method of claim 11 wherein a plurality of EEG electrodes are employed and the comparisons of (d) are displayed in a display corresponding to the locations of the EEG electrodes and displaying graphic trajectories representing changes in brain wave states at each EEG electrode.

17. The method of claim 11 wherein the warning is a visual signal on a computer system monitor screen.

18. The method of claim 11 wherein the warning is a vibratory signal delivered by a wristband.

19. An electroencephalograph (EEG) method for monitoring the plane of anesthesia of a patient undergoing a medical procedure, comprising:

(a) removably connecting an EMG (electromyograph) and an EEG (electroencephalograph) electrode to the front of the scalp of the patient and administering sufficient anesthesia to the patient for the patient to attain the plane of anesthesia selected by the anesthesiologist;

(b) amplifying and digitizing the brainwaves in the Beta 2 band from the EEG electrode and amplifying and digitizing the patient's facial muscle activity from the EMG electrode to provide a set of digital data representing the patient's brain waves in the Beta 2 band and facial muscle activity during the patient's pre-operative anesthetized state and displaying said first set to the anesthesiologist;

(c) providing a warning if the patient shows too much facial muscle activity and brain wave activity in the Beta band prior to or during the operation indicating insufficient anesthesia;

(d) adjusting the anesthesia administered to the patient in response to a warning to decrease the anesthesia and yet maintain the patient at the selected plane of anesthesia.

20. An electroencephalograph (EEG) method for monitoring the plane of anesthesia of a patient undergoing a medical procedure, comprising:

(a) removably connecting a plurality of EEG electrodes to the scalp of the patient;

(b) amplifying and digitizing the patient's ongoing brain wave activity collected from the EEG electrodes to provide a first set of digital data representing mean total EEG power in the patient's pre-operative and pre-anesthetized state;

(c) administering sufficient anesthesia to the patient for the patient to attain the plane of anesthesia selected by the anesthesiologist;

(d) and after (c), digitizing the patient's ongoing brain wave activity to provide a second set of digital data representing mean total EEG power;

(e) using the computer system to statistically compare the first and second sets of digital data;

(f) providing a warning of burst suppression indicating an excess of anesthesia if the mean total power of the second set is significantly below the mean total power of the first set based on the comparison of (d); and (g) administering less anesthesia to the patient in response to the warning.

21. An electroencephalograph (EEG) method for monitoring the plane of anesthesia of a patient undergoing a medical procedure, comprising:

(a) removably connecting an EMG (electromyograph) and EEG (electroencephalograph) electrode to the front of the scalp of the patient and administering sufficient anesthesia to the patient for the patient to attain the plane of anesthesia selected by the anesthesiologist;

(b) amplifying and digitizing the brainwaves in the Beta 2 band from the EEG electrode and amplifying and digitizing the patient's facial muscle activity from the EMG electrode to provide a first set of digital data representing a set of facial muscle activity during the patient's pre-operative anesthetized state and recording the first set of digital data in computer system memory;

(c) during the operation, amplifying and digitizing the brain wave responses in the Beta 2 band from the EEG electrode and the patient's facial muscle activity from the EMG electrode to provide a second set of digital data;

(d) using the computer system to statistically compare the first and second sets of digital data;

(e) providing a warning if the patient shows excessive muscle activity during the operation indicting insufficient anesthesia based on the comparison of (d); and (f) adjusting the anesthesia administered to the patient during the operation in response to the warning to decrease the anesthesia and yet maintain the patient at the selected plane of anesthesia.

22. An electroencephalograph (EEG) method for monitoring the plane of anesthesia of a patient undergoing a medical procedure, comprising:

(a) removably connecting a plurality of EEG electrodes to the scalp of the patient and administering sufficient anesthesia to the patient for the patient to attain the plane of anesthesia selected by the anesthesiologist;

(b) amplifying and digitizing the patient's ongoing brain wave activity collected from the EEG electrodes to provide a first set of digital data representing mean total EEG power in the patient's pre-operative anesthetized state and recording the first set of digital data in computer system memory;

(c) before or during the operation, amplifying and digitizing the patient's ongoing brain wave activity to provide a second set of digital data presenting mean total EEG power;

(d) using the computer system to statistically compare the first and second sets of digital data;

(e) providing a warning of burst suppression indicating an excess of anesthesia if the mean total power of the second set is significantly below the mean total power of the first set based on the comparison of (d); and (f) administering less anesthesia to the patient in response to the warning.

23. An electroencephalograph (EEG) method for monitoring the plane of anesthesia of a patient undergoing a medical procedure, comprising:

(a) removably connecting a plurality of EEG electrodes to the scalp of the patient, connecting a plurality of EKG electrodes to the chest of the patient, connecting at least one blood pressure (BP) sensor to the patient, connecting at least one respiration sensor to the patient, and administering sufficient anesthesia to the patient for the patient to attain the plane of anesthesia selected by the anesthesiologist;

(b) amplifying and digitizing the patient's ongoing brain wave activity collected from the EEG electrodes, the patient's heart beat rate from the EKG electrodes, the patient's blood pressure from the blood pressure sensor and the patient's respiration from the respiration sensor to provide in each case a self-norm comprising a first set of digital data representing the patient's pre-operative anesthetized state and, in each case, recording the first set of digital data in computer system memory;

(c) before or during the operation, amplifying and digitizing the patient's ongoing brain wave activity, EKG, BP and respiration to provide, in each case, a second set of digital data representing total EEG power, EKG, BP and respiration;

(d) using the computer system to statistically, in each case, to compare the first and second sets of digital data;

(e) providing a warning indicating an excess or lack of anesthesia if, in each case, the second set deviates significantly from the first set based on the comparison of (d); and (f) administering less or more anesthesia to the patient in response to the warning.

24. An electroencephalograph (EEG) method for monitoring the plane of anesthesia of a patient undergoing a medical procedure, comprising:

(a) removably connecting a set of EEG electrodes to the scalp of the patient;

(b) amplifying and digitizing the patient's brain wave activity collected from the EEG electrodes to provide a set of digital data and recording the set of digital data in a memory component of a computer system;

(c) using the computer system to extract a set of neurometric features from the digital data;

(d) removing artifacts from the set of neurometric features;

(e) using the computer system to convert the features by a transformation into a normalized statistical score;

(f) developing a discriminant score by applying a plurality of predetermined weighting factors to the normalized statistical scores and summing the products;

(g) converting the discriminant score to a patient state index (PSI) using probability functions;

(h) displaying the patient state index (PSI) on a monitor;

(i) repeating steps (b) through (h) at predetermined intervals and displaying the patient state index (PSI) in a time ordered sequence on the monitor;

(j) administering anesthesia to the patient so as to attain a plane of anesthesia selected by an anesthesiologist;

(k) performing steps (a) to (h) while the patient is at the selected plane of anesthesia of (i) to develop and display a patient state index (PSI) which is a self-norm of the patient at the selected plane of anesthesia;

(l) repeating steps (a)–(h) during the medical procedure and after step (j) while the patient is anesthetized to develop and display the patient state index; and (m) providing more or less anesthesia to the patient in response to statistically significant changes of the PSI in step (l) compared to the self-norm of step (k).

25. The method of claim 24 and in step (b) amplifying and digitizing the patient's ongoing brain wave activity.

26. The method of claim 25 wherein in step (e) the transformation is a logarithmic transformation and the normalized statistical score is a Z-score.

27. The method of claim 24 and in step (b) providing evoked potential stimuli to a patient and amplifying and digitizing the patient's evoked brain wave activity.

28. The method of claim 24 and obtaining a self-norm of the patient prior to administering anesthesia to the patient by performing steps (a)–(h) prior to administration of anesthesia.

29. The method of claim 24 and in (d) removing artifacts by rejection of epochs of digital data in which (i) an EEG signal is too high, (ii) an epoch contains sharp waves, (iii) the voltage of an epoch is under a predetermined voltage, and (iv) an epoch contains a large voltage excursion.

* * * * *